(12) United States Patent
Lowe et al.

(10) Patent No.: US 10,500,019 B2
(45) Date of Patent: Dec. 10, 2019

(54) SYSTEM AND METHOD FOR CORRECTING MALOCCLUSION

(71) Applicant: ORTHOACCEL TECHNOLOGIES, INC., Bellaire, TX (US)

(72) Inventors: Michael Kenneth Lowe, Houston, TX (US); Christopher Lyle Wasden, Sugar Land, TX (US); William Brent Tarver, Houston, TX (US)

(73) Assignee: OrthoAccel Technologies, Inc., Bellaire, TX (US)

( * ) Notice: Subject to any disclaimer, the term of this patent is extended or adjusted under 35 U.S.C. 154(b) by 0 days.

(21) Appl. No.: 15/892,187

(22) Filed: Feb. 8, 2018

(65) Prior Publication Data
US 2018/0168774 A1   Jun. 21, 2018

Related U.S. Application Data

(63) Continuation of application No. 13/609,346, filed on Sep. 11, 2012, now Pat. No. 9,943,380, which is a
(Continued)

(51) Int. Cl.
*A61C 7/00* (2006.01)
*A61C 7/08* (2006.01)

(52) U.S. Cl.
CPC ............. *A61C 7/00* (2013.01); *A61C 7/008* (2013.01); *A61C 7/08* (2013.01); *A61C 7/002* (2013.01)

(58) Field of Classification Search
CPC .. A61C 7/008; A61C 7/08; A61C 7/00; A61C 7/36; A61C 7/002; A61C 19/063; G06F 19/322
(Continued)

(56) References Cited

U.S. PATENT DOCUMENTS 1,826,434 A * 10/1931 Reiss ..................... A61C 17/20
                                                   601/86
2,253,514 A    8/1941 Fisher
(Continued)

FOREIGN PATENT DOCUMENTS

EP    1 280 261 A1    1/2003
EP    1897609 A2      3/2008
(Continued)

OTHER PUBLICATIONS

*Propel Orthodontics, LLC* v. *OrthQAccel Technologies, Inc.*, Inter Partes Review, U.S. Pat. No. 9,662,184, Case No. IPR2018-00296, Petition for Inter Partes Review with Exhibits 1001-1022, 1,597 pages.
(Continued)

*Primary Examiner* — Matthew M Nelson
(74) *Attorney, Agent, or Firm* — Foley & Lardner LLP

(57) ABSTRACT

Methods of inducing tooth movement and treating malocclusion include reducing orthodontic treatment duration by daily applying cyclic forces simultaneously to teeth of the maxillary and mandibular arches during a treatment period. The teeth are also receiving static forces generated by an orthodontic appliance during the treatment period. The cyclic forces applied daily by clamping the teeth down on a bite plate, and activating an extraoral vibration source configured to deliver the cyclic forces to the bite plate at a constant frequency and a maximum force. Data indicating usage duration and usage frequency is stored electronically.

20 Claims, 12 Drawing Sheets

Related U.S. Application Data continuation-in-part of application No. 12/615,049, filed on Nov. 9, 2009, now Pat. No. 9,028,250, which is a continuation-in-part of application No. 11/773,849, filed on Jul. 5, 2007, now Pat. No. 9,668,828.

(60) Provisional application No. 60/906,807, filed on Mar. 14, 2007.

(58) Field of Classification Search
USPC .................... 433/6, 18, 24, 118, 119, 122
See application file for complete search history.

(56) References Cited

U.S. PATENT DOCUMENTS

| | | | |
|---|---|---|---|
| 2,503,924 A | 4/1950 | Stacery | |
| 2,675,005 A | 4/1954 | Smith | |
| 3,763,869 A | 10/1973 | Sanders | |
| 4,038,571 A | 7/1977 | Hellenkamp | |
| 4,123,844 A * | 11/1978 | Kurz | A61C 7/008 |
| | | | 433/5 |
| 4,148,309 A | 4/1979 | Reibel | |
| 4,244,688 A | 1/1981 | Kurz | |
| 4,348,177 A | 9/1982 | Kurz | |
| 4,348,178 A | 9/1982 | Kurz | |
| 4,382,780 A | 5/1983 | Kurz | |
| 4,727,276 A * | 2/1988 | Izukawa | H02N 2/142 |
| | | | 310/316.02 |
| 4,764,111 A * | 8/1988 | Knierim | A61C 7/00 |
| | | | 340/309.7 |
| 4,883,046 A | 11/1989 | Fontenot | |
| 4,993,413 A | 2/1991 | McLeod et al. | |
| 5,030,098 A * | 7/1991 | Branford | A61H 23/00 |
| | | | 433/215 |
| 5,103,806 A | 4/1992 | McLeod et al. | |
| 5,133,661 A | 7/1992 | Euvrard | |
| 5,191,880 A | 3/1993 | McLeod et al. | |
| 5,238,404 A | 8/1993 | Andreiko | |
| 5,246,367 A | 9/1993 | Ito et al. | |
| 5,259,762 A | 11/1993 | Farrell | |
| 5,263,218 A | 11/1993 | Giuliani et al. | |
| 5,268,396 A | 12/1993 | Lai | |
| 5,269,686 A | 12/1993 | James | |
| 5,273,028 A | 12/1993 | McLeod et al. | |
| 5,314,333 A | 5/1994 | Irmer et al. | |
| 5,362,311 A | 11/1994 | Amino et al. | |
| 5,376,065 A | 12/1994 | McLeod et al. | |
| 5,423,427 A | 6/1995 | Brown | |
| 5,476,333 A | 12/1995 | Matthews | |
| 5,496,256 A * | 3/1996 | Bock | A61C 8/00 |
| | | | 433/174 |
| 5,554,971 A | 9/1996 | Foster et al. | |
| 5,609,482 A | 3/1997 | Pedersen et al. | |
| 5,639,238 A | 6/1997 | Fishburne, Jr. | |
| 5,655,906 A | 8/1997 | Coss et al. | |
| 5,735,298 A | 4/1998 | Mayne et al. | |
| 5,774,425 A * | 6/1998 | Ivanov | A61C 7/00 |
| | | | 368/11 |
| 5,780,958 A | 7/1998 | Strugach et al. | |
| 5,967,784 A * | 10/1999 | Powers | A61C 7/00 |
| | | | 433/2 |
| 5,997,490 A | 12/1999 | McLeod et al. | |
| 6,022,349 A | 2/2000 | McLeod et al. | |
| 6,032,677 A | 3/2000 | Blechman et al. | |
| 6,049,156 A * | 4/2000 | Yamamoto | H02N 2/14 |
| | | | 310/316.01 |
| 6,089,864 A * | 7/2000 | Buckner | A61F 5/56 |
| | | | 433/6 |
| 6,158,439 A | 12/2000 | Streetman | |
| 6,171,312 B1 | 1/2001 | Beaty | |
| 6,222,301 B1 * | 4/2001 | Sakai | H02N 2/14 |
| | | | 310/316.01 |
| 6,234,975 B1 | 5/2001 | McLeod et al. | |
| 6,276,931 B1 | 8/2001 | DeLeo | |
| 6,353,956 B1 | 3/2002 | Berge | |
| 6,384,511 B1 * | 5/2002 | Sakai | H02N 2/14 |
| | | | 310/316.01 |
| 6,507,172 B2 | 1/2003 | Sherman | |
| 6,539,249 B1 | 3/2003 | Kadhiresan et al. | |
| 6,561,991 B2 | 5/2003 | McLeod et al. | |
| 6,607,497 B2 | 8/2003 | McLeod et al. | |
| 6,611,780 B2 | 8/2003 | Lundell et al. | |
| 6,613,001 B1 * | 9/2003 | Dworkin | A61C 7/00 |
| | | | 600/590 |
| 6,632,088 B2 | 10/2003 | Voudouris | |
| 6,633,747 B1 * | 10/2003 | Reiss | A61C 7/00 |
| | | | 340/384.1 |
| 6,648,639 B2 | 11/2003 | Mao | |
| 6,790,039 B1 | 9/2004 | Bowen | |
| 6,832,912 B2 * | 12/2004 | Mao | A61C 7/22 |
| | | | 433/24 |
| 6,843,776 B2 | 1/2005 | Trandafir et al. | |
| 6,870,304 B2 | 3/2005 | Magnussen et al. | |
| 6,884,227 B2 | 4/2005 | Krompasick | |
| 6,899,715 B1 | 5/2005 | Beaty | |
| 7,029,276 B2 * | 4/2006 | Mao | A61C 7/00 |
| | | | 433/24 |
| 7,163,399 B2 | 1/2007 | Kajimoto et al. | |
| 7,166,067 B2 | 1/2007 | Talish et al. | |
| 7,192,281 B2 | 3/2007 | Mailyan | |
| 7,207,954 B2 | 4/2007 | Trandafir et al. | |
| 7,207,955 B2 | 4/2007 | Krompasick | |
| 7,210,483 B1 | 5/2007 | Lesniak et al. | |
| 7,212,958 B2 | 5/2007 | Ascenzi et al. | |
| 7,296,318 B2 * | 11/2007 | Mourad | A46B 15/0002 |
| | | | 15/22.1 |
| 7,409,741 B2 | 8/2008 | Dworzan | |
| 7,511,454 B1 | 3/2009 | Legg | |
| 8,037,883 B2 | 10/2011 | Engel | |
| 8,123,520 B2 | 2/2012 | Yamamoto et al. | |
| 8,152,521 B2 | 4/2012 | Yamamoto et al. | |
| 8,500,446 B2 | 8/2013 | Lowe | |
| 8,939,762 B2 | 1/2015 | Lowe | |
| 9,028,250 B2 | 5/2015 | Spaulding et al. | |
| 9,370,405 B2 | 6/2016 | Lowe | |
| 9,370,406 B2 | 6/2016 | Lowe | |
| 9,662,183 B2 | 5/2017 | Lowe et al. | |
| 9,662,184 B2 | 5/2017 | Lowe | |
| 9,668,828 B2 | 6/2017 | Lowe et al. | |
| 9,700,384 B2 | 7/2017 | Lowe | |
| 9,827,082 B2 | 11/2017 | Lowe et al. | |
| 9,848,959 B2 | 12/2017 | Lowe et al. | |
| 2002/0072029 A1 | 6/2002 | Mao | |
| 2002/0077567 A1 | 6/2002 | McLeod et al. | |
| 2002/0077570 A1 | 6/2002 | McLeod et al. | |
| 2002/0166493 A1 | 11/2002 | Sorensen | |
| 2003/0182745 A1 | 10/2003 | Hartman et al. | |
| 2003/0216899 A1 | 11/2003 | Ascenzi et al. | |
| 2004/0013993 A1 * | 1/2004 | Ito | A61C 7/00 |
| | | | 433/6 |
| 2004/0062786 A1 | 4/2004 | Ascenzi et al. | |
| 2004/0063073 A1 * | 4/2004 | Kajimoto | A61C 8/0006 |
| | | | 433/215 |
| 2004/0067833 A1 | 4/2004 | Talish et al. | |
| 2004/0101800 A1 | 5/2004 | Mao | |
| 2004/0101801 A1 | 5/2004 | Mao | |
| 2004/0191720 A1 | 9/2004 | Coopersmith | |
| 2004/0244805 A1 | 12/2004 | Cook et al. | |
| 2004/0265769 A1 | 12/2004 | Inman | |
| 2005/0037315 A1 | 2/2005 | Inoue et al. | |
| 2005/0131662 A1 | 6/2005 | Ascenzi et al. | |
| 2005/0202363 A1 * | 9/2005 | Osterwalder | A61C 9/0006 |
| | | | 433/29 |
| 2005/0255427 A1 | 11/2005 | Shortt et al. | |
| 2005/0283072 A1 | 12/2005 | Qin et al. | |
| 2006/0014121 A1 | 1/2006 | DelGrosso | |
| 2006/0052844 A1 * | 3/2006 | Newman | A61N 1/323 |
| | | | 607/67 |
| 2006/0115785 A1 | 6/2006 | Li et al. | |
| 2006/0166157 A1 * | 7/2006 | Rahman | A61B 5/4833 |
| | | | 433/6 |
| 2006/0172262 A1 | 8/2006 | Bruce | |

(56) References Cited

U.S. PATENT DOCUMENTS

| | | |
|---|---|---|
| 2006/0287620 A1 | 12/2006 | Tseng |
| 2007/0009851 A1 | 1/2007 | Kilcher et al. |
| 2007/0038165 A1 | 2/2007 | Trandafir et al. |
| 2007/0040529 A1 | 2/2007 | Takebayashi et al. |
| 2007/0043310 A1 | 2/2007 | Trandafir et al. |
| 2007/0055185 A1 | 3/2007 | Trandafir et al. |
| 2007/0065768 A1* | 3/2007 | Nadav .................. A61C 7/006 433/6 |
| 2007/0103016 A1 | 5/2007 | Park et al. |
| 2007/0161461 A1 | 7/2007 | Nguyen |
| 2007/0161931 A1 | 7/2007 | Kunita |
| 2007/0179414 A1 | 8/2007 | Imboden et al. |
| 2007/0208284 A1 | 9/2007 | Huang |
| 2007/0255188 A1 | 11/2007 | Tseng |
| 2007/0260296 A1* | 11/2007 | Porter .................. A61N 5/062 607/88 |
| 2007/0276197 A1* | 11/2007 | Harmon ................ G06F 19/00 600/300 |
| 2007/0299372 A1 | 12/2007 | Chang |
| 2008/0032899 A1 | 2/2008 | Caritey et al. |
| 2008/0032248 A1 | 4/2008 | Kuo |
| 2008/0129130 A1 | 6/2008 | Mun et al. |
| 2008/0217391 A1* | 9/2008 | Roof ................... G06F 19/3462 235/375 |
| 2008/0227046 A1 | 9/2008 | Lowe et al. |
| 2008/0227047 A1 | 9/2008 | Lowe et al. |
| 2008/0233541 A1* | 9/2008 | De Vreese ........... A61C 19/003 433/216 |
| 2008/0243038 A1* | 10/2008 | Bennett .............. A63B 24/0075 601/33 |
| 2008/0273391 A1* | 11/2008 | Steedman .............. G11C 5/147 365/185.18 |
| 2008/0283422 A1 | 11/2008 | Jansheski |
| 2009/0042159 A1 | 2/2009 | Yamamoto et al. |
| 2009/0051312 A1 | 2/2009 | Simon et al. |
| 2009/0058361 A1 | 3/2009 | John |
| 2009/0061375 A1 | 3/2009 | Yamamoto et al. |
| 2009/0061379 A1 | 3/2009 | Yamamoto et al. |
| 2009/0061380 A1 | 3/2009 | Yamamoto et al. |
| 2009/0105523 A1 | 4/2009 | Kassayan et al. |
| 2009/0123965 A1 | 5/2009 | Wahl |
| 2009/0155740 A1 | 6/2009 | Jensen et al. |
| 2009/0224616 A1 | 9/2009 | An |
| 2009/0305184 A1 | 12/2009 | Ting et al. |
| 2010/0042441 A1* | 2/2010 | Steusloff ................ G06F 3/002 705/3 |
| 2010/0055634 A1 | 3/2010 | Spaulding et al. |
| 2010/0092916 A1 | 4/2010 | Teixeira et al. |
| 2010/0109644 A1 | 5/2010 | Pruckner et al. |
| 2010/0286698 A1 | 11/2010 | Del Rio et al. |
| 2011/0136070 A1 | 6/2011 | Rubin et al. |
| 2011/0136071 A1 | 6/2011 | Levens |
| 2011/0229848 A1 | 9/2011 | Hertz |
| 2012/0048274 A1 | 3/2012 | Bayron et al. |
| 2012/0322018 A1 | 12/2012 | Lowe et al. |
| 2013/0029505 A1 | 1/2013 | Hackett et al. |
| 2013/0059263 A1* | 3/2013 | Lowe ................... A61C 7/00 433/6 |
| 2013/0095446 A1* | 4/2013 | Andreiko .............. A61C 7/08 433/6 |
| 2013/0122448 A1* | 5/2013 | Kitching ............... A61C 7/002 433/24 |
| 2013/0252193 A1* | 9/2013 | Bowman ............... A61C 7/08 433/6 |
| 2013/0266906 A1* | 10/2013 | Soo ..................... A61C 7/10 433/6 |
| 2013/0273490 A1* | 10/2013 | Way .................... A61C 7/008 433/6 |
| 2013/0280671 A1* | 10/2013 | Brawn ................ A61N 5/0603 433/24 |
| 2014/0004476 A1* | 1/2014 | Matty ................... A61C 7/08 433/6 |
| 2014/0080082 A1 | 3/2014 | Lowe |
| 2014/0080084 A1* | 3/2014 | Soo ..................... A61C 7/00 433/7 |
| 2015/0079533 A1 | 3/2015 | Lowe |
| 2015/0125806 A1* | 5/2015 | Miller .................. A61C 7/00 433/24 |
| 2015/0173856 A1 | 6/2015 | Lowe et al. |
| 2015/0224305 A1* | 8/2015 | Davidovitch .......... A61N 1/205 433/6 |
| 2015/0231179 A1* | 8/2015 | Sahin ................... A61K 35/28 433/24 |
| 2016/0081768 A1* | 3/2016 | Kopelman ............ A61C 7/10 433/6 |
| 2016/0184054 A1 | 6/2016 | Lowe |

FOREIGN PATENT DOCUMENTS

| | | |
|---|---|---|
| JP | 2001-340412 A | 12/2001 |
| JP | 2003-120577 A | 4/2003 |
| JP | 2004-321498 A | 11/2004 |
| JP | 2007-260158 A | 10/2007 |
| WO | WO-2001/078217 A1 | 10/2001 |
| WO | WO-2005092234 A1 | 10/2005 |
| WO | WO-2007116654 A1 | 10/2007 |
| WO | WO-2007/146187 A2 | 12/2007 |
| WO | WO-2007146703 A2 | 12/2007 |
| WO | WO-2009/123965 A1 | 10/2009 |
| WO | WO-2009158297 A1 | 12/2009 |

OTHER PUBLICATIONS

*Propel Orthodontics, LLC v. OrthoAccel Technologies, Inc.*, Inter Partes Review, U.S. Pat. No. 9,682,184, Case No. IPR2018-00398, Petition for Inter Partes Review with Exhibits 1001-1014 1,448 pages.

Kau, et al., The clinical evaluation of a novel cyclical force generating device in orthodontics, Orthodontic 1(1):43-44 (2010).

Chatoo A., Good Vibrations: Technology Meets Orthodontics, PPD Jul. 2011: 125-129.

Krishtab SI, Doroshenko SI, Liutik GI, [Use of vibrating action on the teeth to accelerate orthodontic treatment], Stomatologiia (Mosk). May-Jun. 1986; 65(3):61-3 {article not provided as we were unable to obtain a copy}.

Marie SS, Powers M, Sheridan JJ., Vibratory stimulation as a method of reducing pain after orthodontic appliance adjustment. J Clin Orthod. Apr. 2003;37(4):205-8 (2003).

Plaintiff OrthoAccel Technologies Inc.'s Original Complaint for Patent Infringement filed Jul. 4, 2017 in *Orthoaccel Technologies, Inc. v. Propel Orthodontics, LLC* and *Propel Orthodontics USA, LLC*, U.S.D.C., Northern District of California, Case No. 5:17-cv-03801.

Plaintiff's Motion for Preliminary Injunction [redacted version] (with Exhibits); [proposed] Order filed Aug. 18, 2017 in *Orthoaccel Technologies, Inc. v. Propel Orthodontics, LLC* and *Propel Orthodontics USA, LLC*, U.S.D.C., Northern District of California. Case No. 5:17-cv-03801.

Defendants Propel Orthodontics, LLC and Propel Orthodontics USA, LLC's Answer (with Exhibits) filed Sep. 11, 2017 in *Orthoaccel Technologies, Inc. v. Propel Orthodontics, LLC* and *Propel Orthodontics USA, LLC*, U.S.D.C., Northern District of California, Case No. 5:17-cv-03801.

Defendants' Opposition to Plaintiffs' Motion for Preliminary Injunction (with Exhibits) [redacted version for public filing] filed Sep. 16, 2017 in *Orthoaccel Technologies, Inc. v. Propel Orthodontics, LLC* and *Propel Orthodontics USA, LLC*, U.S.D.C., Northern District of California, Case No. 5:17-cv-03801.

Plaintiff's Reply in Support of its Motion for Preliminary Injunction filed Sep. 28, 2017 in *Orthoaccel Technologies, Inc. v. Propel Orthodontics, LLC* and *Propel Orthodontics USA, LLC*, U.S.D.C., Northern District of California, Case No. 5:17-cv-03801.

Defendants' Objection to Reply Evidence and Administrative Motion For Leave to File Sur-Reply to Plaintiff's Reply [in Support of its Motion for Preliminary Injunction]; [proposed] Order filed Oct. 4, 2017 in *Orthoaccel Technologies, Inc. v. Propel Orthodontics, LLC*

(56) References Cited

OTHER PUBLICATIONS and *Propel Orthodontics USA, LLC*, U.S.D.C., Northern District of California, Case No. 5:17-cv-03801.
Defendants' Administrative Motion Notifying Court of Recent Office Action by the United States Patent and Trademark Office filed Nov. 3, 2017 in *Orthoaccel Technologies, Inc.* v. *Propel Orthodontics, LLC* and *Propel Orthodontics USA, LLC*, U.S.D.C., Northern District of California, Case No. 5:17-cv-03801.
Plaintiff's Response Regarding Defendants' Administrative Motion Notifying Court of Recent Office Action by the United States Patent and Trademark Office filed Nov. 6, 2017 in *Orthoaccel Technologies, Inc.* v, *Propel Orthodontics, LLC* and *Propel Orthodontics USA, LLC*, U.S.D.C., Northern District of California, Case No. 5:17-cv-03801.
H8/300L Precise Control of DC Motor (DCmotor), Mar. 2004, Renesas.
Shimizu, "A study of the Movement of the Lateral Incisor of the Macata fuscata loaded by a vibrating force," Journal of Japan Orthodontic Society. 45:56-72 (1986).
El-Baily T., Cutting Teeth, Research News; Alberta Heritage Foundation for Medical Research; Spring 2007.
Al-Mubarak, Rasha, et al., Expression and Mechanical Modulation of Matrix Metalloproteinase-1 and -2 Genes in Facial and Cranial Sutures, Cell Tissue Res. (2005) 321:465-471.
Collins John et al., Expression of Matrix Metalloproteinase Genes in the Rat Intramembranous Bone During Postnatal Growth and Upon Mechanical Stresses, Journal of Biomechanics 38 (2005) 485-492.
Tang, Minghui, et al., Matrix and Gene Expression in the Rat Cranial Base Growth Plate, Cell Tissue Res (2006) 324:467-474.
Wang X., et al., Chondrocyte Proliferation of the Cranial Base Cartilage Upon in vivo Mechanical Stresses, J. Dent. Res. (2002)81(10): 701-705.
Mao JJ., Calvarial Development: Cells and Mechanics, Current Opinion in Orthopaedics (2005), 16:000-000.
Kopher, Ross et al., Suture Growth Modulated by the Oscillatory Component of Micromechanical Strain, Journal of Bone and Mineral Research (2003)(vol. 18, No. 3.
Mao JJ., Mechanobiology of Craniofacial Sutures, J. Dent Res (2002) 81(12): 810-816.
Kopher, Ross et al., Expression of in vivo Mechanical Strain Upon Different Wave Forms of Exogenous Forces in Rabbit Craniofacial Sutures, Annals of Biomedical Engineering (2003) vol. 31, pp. 1125-1131.
Mao JJ., et al, Growth and Development: Hereditary and Mechanial Modulations, American Journal of Orthodontics and Dentofacial Orthopedica, vol. 125, No. 6, Jun. 2004.
Peptan, Alexandra et al., Responses of Intramembranous Bone and Sutures Upon in vivo Cyclic Tensile and Compressive Loading, Bone (2007), doi: 10.1016/j.bone.2007.05.014.
Kapil, Vij et al., Geometry and Cell Density of Rat Craniofacial Sutures During Early Postnatal Development and Upon in vivo cyclic loading, Bone 38 (2006) 722-730.
Kapil, Vij, Developmental Changes in Rat Craniofacial Sutures Following Mechanical Stimulation, Thesis University of Illinois at Chicago, 2004, vol. 94, Chp. 2.
Shapiro, E. et al., Orthodontic Movement Using Pulsating Force-Induced Piezoelectricity; Am. J. Orthod., Jul. 1979, pp. 59-66.
Declaration of Dr. Sumit Yadav in Support of Petition for Inter Partes Review of U.S. Pat. No. 9,662,184 in *Propel Orthodontics, LLC* v. *OrthoAccel Technologies, Inc.*, Case No. IPR2018-00296, dated Dec. 14, 2017, 65 pages.
Kincade, Kathy, "Vibration Therapy Speeds Tooth Movement," Dental News, Dental Education, Dental Social Networking, dated Sep. 21, 2009, http://www.drbicuspid.com/index.aspx?sec=ser&sub=def&pag=dis&itemID=302804, 4 pages.
Mao, Jeremy J,, "Advances in Orthodontic Treatment," Sep. 2009, 11 pages.
Micromo, DC Motor Application Considerations, 2008, http://micromo.com/dc-motor-application-considerations.aspx.
Renesas, H8/300L Precise Control of DC Motor (DCmotor), Mar. 2004.
Krishtab SI, Doroshenko SI, Liutik GI, [Use of vibrating action on the teeth to accelerate orthodontic treatment], Stomatologiia (Mosk). May-Jun. 1986; 65(3):61-3 (machine translation in English and copy in Russian).
Peptan, Alexandra et al., Responses of Intramembranous Bone and Sutures Upon in vivo Cyclic Tensile and Compressive Loading, Bone 42 (2008) 432-438 (published online Jun. 7, 2017).
Decision entered Jul. 15, 2018 by U.S. Patent & Trademark Office, Patent Trial and Appeal Board in *Propel Orthodontics, LLC* v. *OrthoAccel Technologies, Inc.*, Case IPR 2018-00398, 30 pages.
Decision entered Jun. 11, 2018 by U.S. Patent & Trademark Office, Patent Trial and Appeal Board in *Propel Orthodontics, LLC* v. *OrthoAccel Technologies, Inc.*, Case IPR 2018-00296, 16 pages.
Order Denying Motion for Preliminary Relief entered Jan. 3, 2018 in *OrthoAccel Technologies, Incv. Propel Orthodontics, LLC* , U.S.D.C., Northen District of California, Case No. 5:17-cv-03801, 9 pages.

\* cited by examiner

SYSTEM AND METHOD FOR CORRECTING MALOCCLUSION

CROSS REFERENCE TO RELATED APPLICATIONS

This application is a continuation of U.S. patent application Ser. No. 13/609,346, filed Sep. 11, 2012, now pending, which is a continuation-in-part of U.S. patent application Ser. No. 12/615,049 filed on Nov. 9, 2009, now U.S. Pat. No. 9,028,250, which is a continuation-in-part of U.S. patent application Ser. No. 11/773,849 filed on Jul. 5, 2007, now U.S. Pat. No. 9,668,828, which claims priority from U.S. Provisional Patent Application Ser. No. 60/906,807, filed on Mar. 14, 2007, the disclosures of which are incorporated herein by reference.

BACKGROUND

This system relates to systems and methods for treating malocclusion.

Orthodontics is a specialty of dentistry that treats malocclusion through the displacement of teeth and control and modification of facial growth. This process is accomplished by using mechanical static forces to induce bone remodeling thereby enabling teeth to move. This widely accepted approach to treating malocclusion takes about twenty four months on average. In this approach, orthodontic braces, consisting of an archwire that applies a continuous static force to the teeth interfaces with brackets that are affixed to each tooth, are used to treat a number of different classifications of clinical malocclusion. These clinical malocclusions include underbites, overbites, cross bites, open bites, and crooked teeth, for both esthetic and functional/structural reasons. Recently, removable clear appliances such as the Invisalign® system have been introduced for treating teeth. The removable appliances, as well as the traditional components of the orthodontic system, for example the tooth brackets and an archwire, are disposable, At an initial visit, during a procedure known as bonding, orthodontic brackets are affixed to the teeth with cement or some similar substance with adhesive properties. With the exception of incidents of damage or loss of brackets, the same brackets are maintained throughout the entire course of treatment. At the end of the treatment, the orthodontic brackets are removed. Archwires are typically changed at adjustment visits as necessary. The previous archwire is disposed of each time a new one is ligated to the brackets. These direct materials are charged to the patient as a cost element of the larger treatment fee, which also includes overhead expenses and direct labor costs. Fixed appliances, such as retainers that must be worn for some duration post-treatment and clear aligners which are worn until a pre-determined subsequent visit, are customized in fit and sold to the patient. Headgear is typically sold to the patient through the orthodontist and represents a fixed and set cost that must be paid regardless of treatment duration.

Orthodontic treatment can be complicated by the fact that it is oftentimes uncomfortable and painful for patients. Medical devices have not alleviated the pain associated with this treatment, including initial bonding, adjustments, and ongoing discomfort between visits. Post-treatment stability of results and tissue integrity are also important considerations related to orthodontic treatment. Stability is typically accomplished and enhanced through ongoing wear of retainers, in many cases indefinitely. Compliance issues in wearing retainers can lead to relapses that require additional treatments.

SUMMARY

Methods of inducing tooth movement and treating malocclusion include reducing orthodontic treatment duration by daily applying cyclic forces simultaneously to teeth of the maxillary and mandibular arches during a treatment period. The teeth are also receiving static forces generated by an orthodontic appliance during the treatment period. The cyclic forces applied daily by clamping the teeth down on a bite plate, and activating an extraoral vibration source configured to deliver the cyclic forces to the bite plate at a constant frequency and a maximum force. Data indicating usage duration and usage frequency is stored electronically.

In one aspect, an orthodontic appliance includes an extraoral vibratory source and an intraoral dentition interface in the form of a bite plate or platform. A device interface couples the extraoral vibratory source to the intraoral attachment.

In another aspect, an orthodontic appliance includes an intraoral vibratory source and an intraoral bite plate or platform that comes into contact with the dentition. A device interface couples the intraoral vibratory source to the intraoral bite plate or platform.

Implementations of the above aspect can include one or more of the following. A bite plate can be coupled to the extraoral or intraoral vibratory source. The bite plate can interact with any surface of the dentition, especially occlusal.

Furthermore, the interface can contact the teeth at any point and at one or more points. A processor can control the extraoral or intraoral vibratory source. The processor runs software that captures usage frequency and duration and can be programmed to change the force, frequency, wave form, amplitude, duration or any other operating parameter. The processor can communicate usage frequency and duration to a remote computer via any type of wired or wireless communication method. The processor can communicate with the remote computer over the Internet. The processor can actively communicate with the user to provide input related to device use, especially related to biting too hard or not hard enough on the bite plate or platform. A mechanism can be provided to measure proper use based on moisture or temperature sensing, or salivary mineral content sensing, and feedback can be provided based on this control parameter as well. A non-rechargeable or rechargeable battery can drive the vibratory source, wherein the rechargeable battery is charged using power from any type of power source including a USB port or an RS-232 port or a FireWire port, for example. The vibratory source can include a motor or a piezoelectric device. A leasing, rental or per procedure usage or any other variable usage systems as well as an out right purchase system enables the extraoral vibratory source to be provided to patients a low cost. The system can provide diagnostic information to a service provider. The system also supports recycling the extraoral vibratory source.

In another aspect, a system for treating malocclusion includes a device that delivers non-static forces to teeth, the device disposed to teeth, and the device can be leased to a treating professional.

In yet another aspect, a system for treating tooth pain includes a device that delivers non-static forces to one or more teeth and where the device disposed to the teeth provides pain relief.

In yet another aspect, a method for recording the compliant use of an orthodontic device that delivers non-static forces to teeth includes a device that delivers non-static forces to teeth, where the device having electronic media that captures information pertaining to delivery.

In a further aspect, a system delivers non-static forces to change dental tissue including a jaw, mandible or maxilla. The jaw receives sustained non-static forces that are then delivered to the teeth constituents, and the non-static forces remodels the tissues of the mandible, maxilla, or jaw. The device can be used for other type of maxillofacial application and trauma like TMJ, Lefort classification procedures, tooth and other dental implants, among others.

In other aspects, inducing tooth movement and treating malocclusion, craniofacial anomalies, bony defects, and dentofacial deformities through accelerated bone remodeling are achieved by the delivery non-static forces; reducing pain and discomfort in patients; and improving tissue integrity long-term results as to prevent post-orthodontic treatment relapse. The methods and apparatus include a mechanism for data capture and analysis related to patient compliance and usage behavior, as well as for establishing the invention as a component of the clinical office workflow to increase efficiency and productivity.

In another aspect, tooth whitening and stain removal are facilitated by using the device as a delivery system for some tooth whitening agent, especially dentifrice and bleaching gel or solution. It is understood that said agent can exist in any form, including strips, composition, and concentration. The bleaching agent can interact directly with the dental tissue and can also percolate through the orthodontic appliances so that it is delivered even underneath the brackets.

In yet another aspect, the orthodontic appliance(s) or dentition can be cleaned via a brushing mechanism. The benefits of such an adjunctive apparatus are two-fold: oral hygiene is improved and compliance across both activities, use of the device for orthodontic benefit, as well as for prophylactic benefit, is enhanced.

Advantages of the system may include one or more of the following. The system enhances the traditional orthodontic treatment process with the application of non static forces. In accordance with one embodiment of the system, non-static forces are used to accelerate the remodeling of craniofacial bones in conjunction with orthodontic treatment. The system can be used to treat all forms and classifications of dental malocclusion, craniofacial anomaly, boney defect, or dentofacial deformity in which bone remodeling plays a physiological role. The system can be used exclusively in the maxilla, exclusively in the mandible, or in a dual-arch manner (both maxilla and mandible at the same time). Furthermore, the system can be used to treat cases presenting with a full dentition, any combination of naturally or unnaturally missing teeth, and to remodel bone in edentulous patients. Patients of any age and medical history profile can be treated. The system can be used by patients taking any type of medication.

The system enables orthodontic treatment and tooth movement to be considered in the broader context of bone remodeling. The rate-limiting step for orthodontic tooth movement is osteogenesis. Dynamic loading (cyclic forces) lead to greater osteogenesis or bone growth/bone remodeling, than static forces. Moving teeth is accomplished by remodeling the surrounding alveolar craniofacial bone. Bone remodeling involves several steps. First, net bone resorption occurs and takes two to three weeks. Second, reversal from net resorption to net formation takes place. Finally, bone formation fills the cavity in three to four months. Osteoclastic activity typically clears the path for tooth movement five to six times faster than osteoblastic activity fills it. Consequently, in order to speed up movement, bone formation (osteogenesis) must speed up.

Certain dynamic loading patterns (higher frequency and inserting rest periods, for example) greatly increase bone formation compared to basic dynamic loading, for example as 1 Hertz sinusoid. Inserting rest periods is known to be especially efficacious as it allows mechanosensitivity to be restored to the bone tissue. A point of diminishing returns is reached within each loading session. Therefore, intermittently loading and uploading with cyclic force can increase the rate of bone formation significantly. The system enables an efficacious, yet quick treatment period of static force that involves rapidly changing the forces on the teeth. This is done without requiring the introduction of piezoelectric currents to the mechanically stressed bone. Patient compliance is greatly enhanced through computer monitoring of usage. Treatment outcomes are directly dependent on how closely the patient follows the instructions of the healthcare professional. The system can be worn for a predetermined period such as approximately twenty minutes daily or any other suitable duration of time, thus the patient can wear the device at home for a modest wear duration. The healthcare professional can measure patient compliance and usage patterns that have occurred between appointments. The measured compliance and application is stored in electronic means, and is available for retrieval by the health care professional; including retrieval over the internet or any other communication medium.

The system supports a business model that allows for a non-disposable component of the orthodontic treatment to be variable and proportional in cost to the duration of the treatment. The device can be disposable or non-disposable. The device can be leased, rented, or purchased on a procedure basis to the patient directly or through the orthodontist or by a third party. The proposed system also increases orthodontic case throughput and therefore office efficiency.

DESCRIPTION

Figure 1:
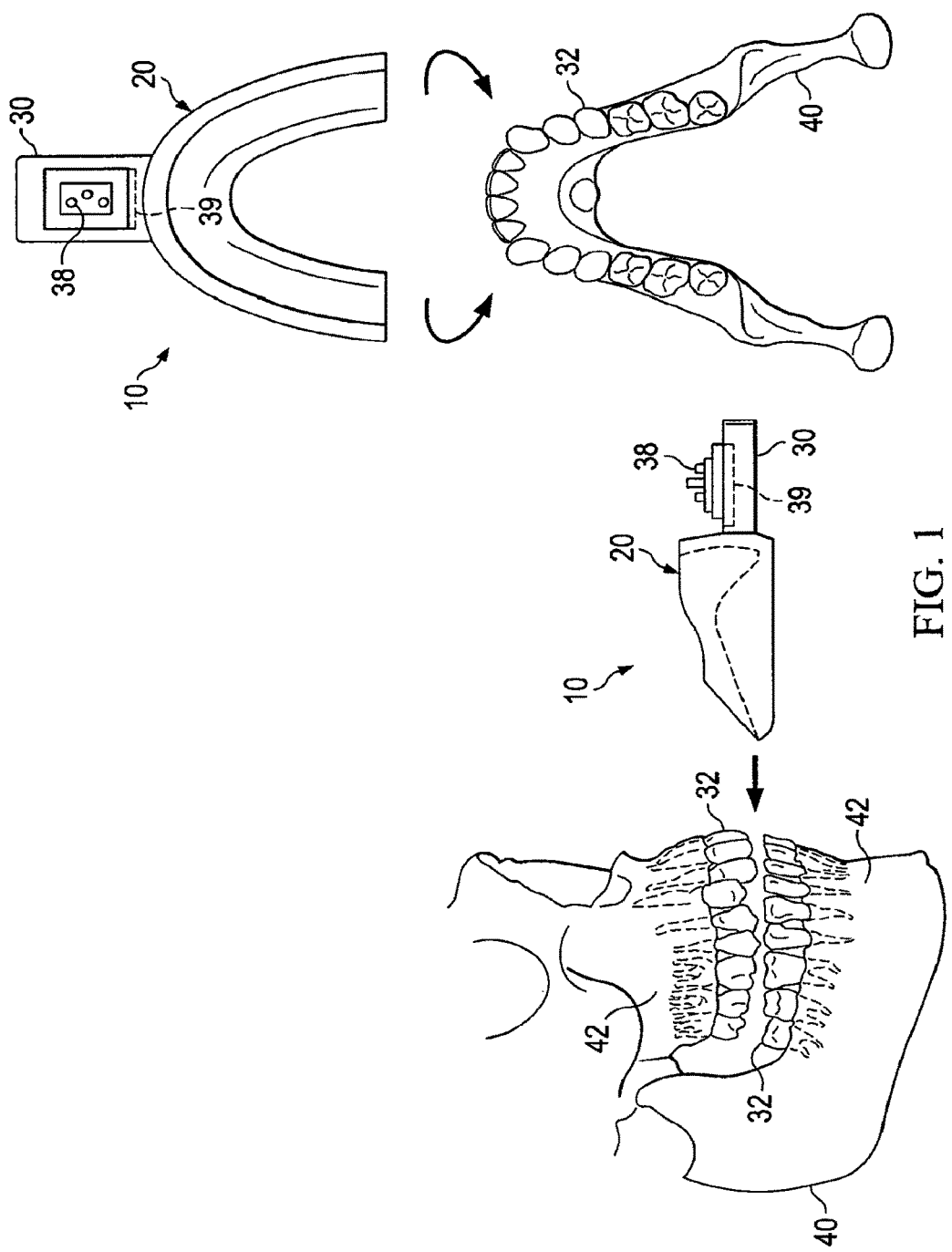
FIG. 1 shows one embodiment of an orthodontic treatment system.

Referring now to the drawings in greater detail, there is illustrated therein structure diagrams for a vibratory dental appliance and logic flow diagrams for the processes a processor will utilize to complete treatment and other dental transactions. It will be understood that the program is run on a computer that is capable of communication with consumers via a network both wired and wirelessly, as will be more readily understood from a study of the diagrams.

In accordance with one embodiment of the invention, non-static forces are used to accelerate the remodeling of craniofacial bones in conjunction with orthodontic treatment. The system can be used to treat all forms and classifications of dental malocclusion, craniofacial anomaly, boney defect, or dentofacial deformity in which bone remodeling plays a physiological role. The system can be used exclusively in the maxilla, exclusively in the mandible, or in a dual-arch manner (both maxilla and mandible at the same time). Furthermore, the system can be used to treat cases presenting with a full dentition, any combination of naturally or unnaturally missing teeth, and to remodel bone in edentulous patients. Patients of any age and medical history profile can be treated. The system can be used by patients taking any type of medication.

FIG. 1 shows one embodiment of an orthodontic treatment system 10. The system or device 10 has an intraoral bite plate 20 that is inserted into a patient's mouth. The bite plate 10 is connected to an extraoral vibration source 30 and interfaces with the dentition 32. The device 10 is clamped down by the patient's jaw 40 on the bite plate 10 to secure the vibration source 30 between the dental arches 42 and to position the system in the patient's mouth. The device 10 can interface with any part of the dentition 32, not being confined to a particular arch, region, quadrant, or tooth, and not being confined to either natural dentition or prosthetic dentition. The vibration source 30 in this embodiment is activated by pushing a button 38 mounted on the extraoral apparatus. The vibration source could be activated by sensing the patient bite pressure as stimuli with a microprocessor 39 or some other mechanism translating the external stimuli into device function, including moisture or temperature sensing as well as salivary mineral content sensing.

Figure 2:
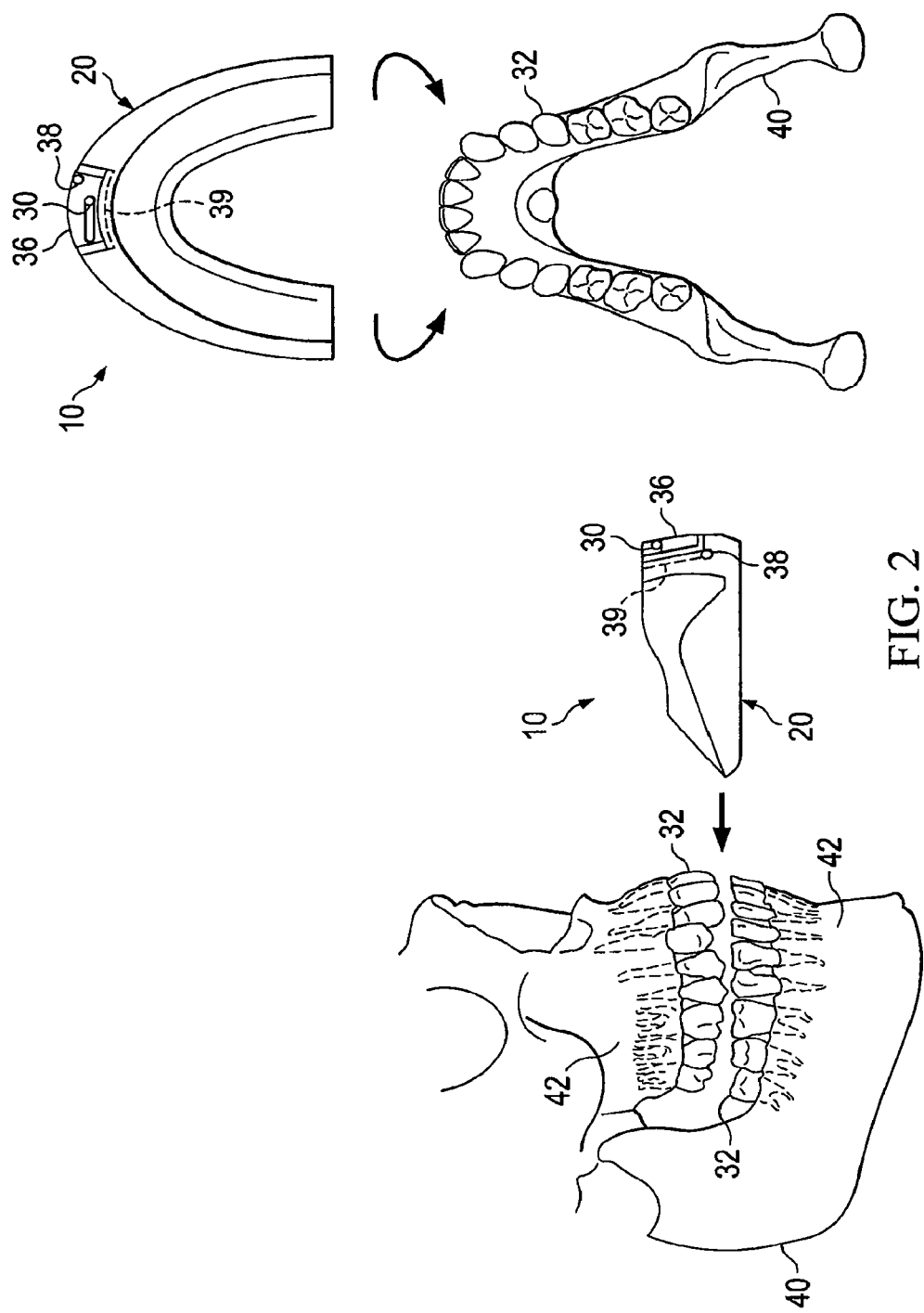
FIG. 2 shows a second embodiment of an orthodontic treatment system.

In another embodiment 10 shown in FIG. 2, the vibration source 30 is positioned intraorally and holds the components necessary to generate and apply the force. This embodiment can generate and apply non-static forces to either the maxillary or mandibular arch or both. This particular embodiment involves a dual arch configuration that works with both dental arches 40. The patient inserts the plate 20 into the oral cavity and bites down, holding the system 10 steady between the teeth, regardless of which of the arches 40 the device is being activated for use with. The vibration source 30 contained in the intraoral compartment 36 is activated by pushing a button 38 mounted to the housing apparatus. The vibration source could be activated by sensing the patient bite pressure as stimuli with a microprocessor 39 or some other mechanism translating the external stimuli into device function.

In one embodiment, the device works when the patient applies sufficient force by biting on the device or otherwise clamping the jaws on the device. This enables the device to control the provision of cyclic forces when the correct amount of force is applied. In this embodiment, the device includes 1) microprocessor and compliance software and reporting system; 2) ability to provide cyclic forces at any level; and 3) the ability to only provide the cyclic force when the teeth apply the correct force on the device. An activation trigger can also be tied to some other stimuli including temperature or moisture sensing as well as salivary mineral content sensing.

Figure 3:
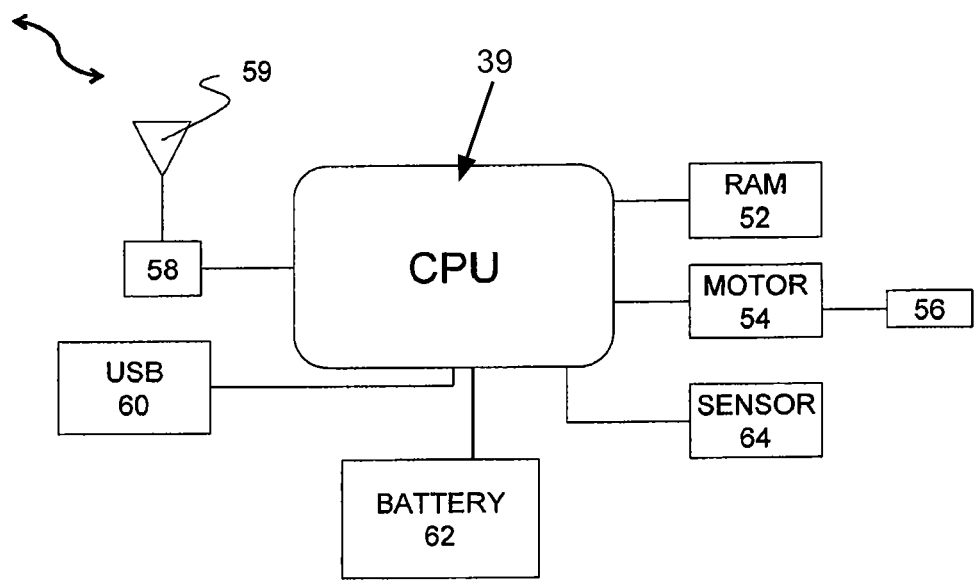
FIG. 3 shows an exemplary diagram of control electronics used with the system of FIGS. 1-2.

FIG. 3 shows an exemplary diagram of control electronics used with the system of FIGS. 1-2. The functional electromechanical components include a processor or microprocessor 39 that can be a low power microcontroller. The processor or microprocessor 39 stores instructions and data in a memory 52. The processor or microprocessor 39 drives the vibration source 30, which is an actuator 54 such as an electrical motor or a piezoelectric device, among others. The system of FIG. 3 receives energy from a battery 62 that can be rechargeable. The processor or microprocessor 39 can be programmed or updated through a communication port 60 such as a USB port. Alternatively, the processor or microprocessor 39 can be wirelessly updated through a wireless transceiver 58 connected to an antenna 59. The battery 62 can be of any type and can be a rechargeable type with a bite plate docking port that recharges the battery upon insertion thereto. The processor or microprocessor 39 can also communicate with an optional sensor 64 to capture patient dental data if needed. The processor or microprocessor 39 can also simply transmit its operational parameters through the communication port 60 or the wireless transceiver 58 so that a dental professional such as a dentist, an orthodontist, a hygienist, a treatment coordinator, a staff member, a patient, or a third party can monitor treatment progress as required.

The vibration source 30 can be an actuator which can include a motor driven bite plate or platform. Upon activation, the plate or platform, which can be of any shape or thickness, and comprised of any material, sufficient to come into and out of contact with the dentition 32, in part or in whole, vibrates in a manner that delivers the necessary force. The device can have one or more interface points across the dentition, or can interface with the entire dentition in aggregate and in both arches simultaneously. This movement in total completes one cycle. The system embodied as the device described here pulsates or vibrates at a frequency of between about 0.1 Hertz to about 400 Hertz.

Although a vibrating plate or platform is discussed above, the means of generating the cyclic forces for delivery to the teeth or dentofacial bone structure can be of any form. In one embodiment, the vibratory source 30 is mechanically or electrically induced. The vibratory source can also apply piezoelectric devices as discussed above. A mechano-transduction pathway can be embedded in the system as well. Furthermore, the embodiment of the system can be fixed, removable, or implantable. The cyclic forces can be also be fluidic in nature.

In one embodiment, the interface with the dentition 32 can transmit a force of about five Newtons (5N) for about twenty minutes a day at a frequency of between 0.1 to 400 Hz, for example up to about 40 Hz. However, the prescribed clinical application of forces can be over any duration, frequency, and time of day combination pattern. Upon completion of one (1) twenty-minute duration of activation, the device automatically shuts off. Pacing indicators in the form of an audible tone, cycle stutter, or by some other means provide feedback to the patient regarding elapsed time and time remaining in the current session of activation. These indicators can be of any form and frequency; the current described system embodies the indicators as one second tones at five-minute intervals for the first fifteen minutes, representing a tone at minute five, minute ten, and minute fifteen; and then a final tone at minute nineteen, indicating that the user has 60 seconds of use remaining. Other indicators and/or suitable treatment intervals can be used to provide notice to the patient. For example, the professional can specify treatment intervals that mixes and matches the usage pattern to get to the 20 minutes such as 4×5 minutes or 10×2 minutes or some other combinations thereof.

After the device shuts off, the patients simply releases bite pressure from the intraoral bite plate and removes the device from the oral cavity. Data capture related to usage frequency and duration updates real time. As such, the device representation of this data post-use will indicate one additional session, and twenty additional minutes in duration of use, as compared to the same device immediately prior to the session.

In one embodiment, the battery 62 is rechargeable and can be inserted into its charger base between uses. Alternatively, the device can embed the battery 62 within its housing, and the entire device is placed into a rechargeable base (or the battery does not require re-charging). The charging of the battery can be done using power from the USB port 60. Alternatively, any suitable computer or electrical connection can be provided to charge the battery. For example, the battery can be charged using RS-232, Firewire, or through a 5V hook. Further, a standard DC converter can be used to charge the battery. The device is hermetically sealed to be airtight and water tight, and can withstand immersion or exposure to water or moisture. It can and should be stored at room temperature. The battery 62 used in this particular embodiment is both memory-free and maintenance-free. The device can have a charger base, or can be inserted just long enough to charge for the next use.

The application of cyclic forces can be used to perform bone modeling and/or remodeling as well as more rapid tooth movement that may occur without bone modeling or remodeling. The bone remodeling and accelerated tooth movement across all types of displacement includes: rotation, translation, intrusion, extrusion, and tipping. This induced accelerated remodeling of bone is relevant for both the alignment and movement of teeth, in any plane, including horizontal and vertical, anterior and posterior, mesial and distal, and facial (buccal and labial) and lingual.

The delivery of the cyclic forces to the teeth and craniofacial bones can be facilitated by contact or any form of interaction with the dentition, including any tooth, group of teeth, or arch. The interface can also include any dental tissue including tissues of the tooth, enamel, dentin, cementum, and pulp, and appliances, especially aligner trays, which can be of any commercial or non-commercial brand or design.

The system can be used in conjunction with lingual braces, facial braces, or any combination across either arch or any quadrant for both. It is also being contemplated as compatible with any robotics-based or other wire-bending optimization technology. The system is also compatible with clear aligner technology treatment plans, including the Invisalign® treatment approach.

The system can be used in conjunction with a new treatment start from the very first appointment at which the orthodontic treatment begins, or it can be slotted into a treatment in progress at any point during the course of the treatment, up to and including the very last clinical stage.

An embodiment of the system can be made available for sale directly to consumers over-the-counter with no orthodontist or healthcare professional involvement. The application being contemplated can be used to both align and mal-align either a single tooth, the entire dentition, or any combination of teeth groups. Teeth being displaced as a result of the non-static forces delivered by this device can include natural teeth without any dental work, natural teeth with dental work including operative restoration of any nature with any material, crown and bridge work, endodontically treated teeth, periodontally treated teeth, teeth surrounded by periodontally treated hard and soft tissue, and any type of dental implant, including micro implants used for orthodontic or tooth movement purposes. The proposed system can be used in conjunction with any type of dental or dentofacial surgery or treatment of trauma to any soft or hard tissue structure.

In another aspect, the system of FIGS. 1-3 can be used in conjunction with any currently used or in-development chemical, biochemical, and tissue engineering treatment approaches to accelerating tooth movement or remodeling craniofacial bone. These treatments may include growth factors, cytokines, matrix metalloproteinases (MMPs), tissue inhibitors of metalloproteinases (TIMPs), and regulation of extracellular matrix molecules. In addition, for both repositioning or stabilizing, tissue remodeling and/or an angiogenic substance(s) can be administered to the patient to promote remodeling of periodontal tissue surrounding the root(s) of the tooth or teeth to be moved. Preferred substance(s) will bind to and activate the relaxin receptor in the tissues which anchor the teeth or other craniofacial structures. Most preferred is relaxin or an analog or mimetic thereof which combines tissue remodeling activity with angiogenic activity. Analogs include peptides, oligomers, fragments, etc. which comprise the active region of native relaxin and mimetics include small molecule drugs, typically below 2 kD, designed to mimic the activity of native relaxin. Alternatively, substance(s) with predominantly angiogenic activity could be selected, such as VEGF, bFGF, estrogen, nitrous oxide, naltrexone, or the like. Further alternatively, collagenases or other tissue-softening enzymes could be utilized to promote periodontal tissue remodeling according to the present invention. In some instances, it may be desirable to combine two or more tissue remodeling and/or angiogenic substance(s) having differing activities. In other instances it may be desirable to deliver different tissue remodeling and/or angiogenic substance(s) at different times during the orthodontic treatment and/or to different regions of the periodontal tissue. The term "relaxin" means human relaxin, including intact full length relaxin or a portion of the relaxin molecule that retains biological activity, as described in U.S. Pat. No. 5,023,321, preferably recombinant human relaxin (H2), and other active agents with relaxin-like activity, such as Relaxin and portions that retain biological activity Like Factor (as described in U.S. Pat. No. 5,911,997), relaxin analogs and portions that retain biological activity (as described in U.S. Pat. No. 5,811,395), and agents that competitively displace bound relaxin from a receptor. Relaxin can be made by any method known to those skilled in the art, for example, as described in any of U.S. Pat. Nos. 5,759,807; 4,835,251 and co-pending U.S. Ser. No. 07/908,766 (PCT US90/02085) and Ser. No. 08/080,354 (PCT US94/0699). More information on applying relaxin to stabilize teeth movement is described in 20040115587 and the foregoing patents, the contents of which are incorporated by reference. It can also be used in conjunction with currently existing, in-development, or emerging treatments related to innovative mechanotherapy, gene therapy, and growth factor delivery. Relevant sutural genetic considerations to the system include genes expressed in development, genes responsible for craniosynostosis/dentofacial deformities, and phenotypes in normal and abnormal development.

Figure 4:
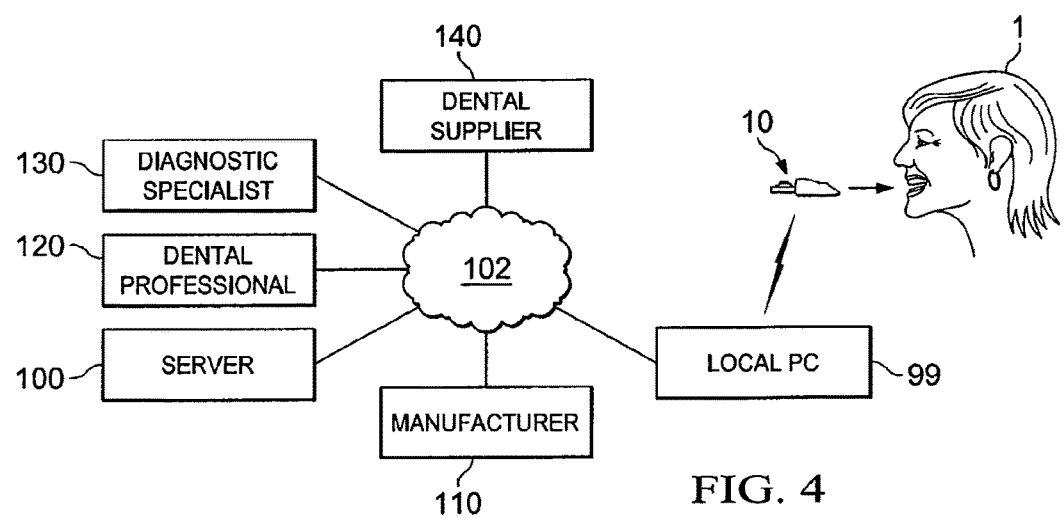
FIG. 4 shows an exemplary dental treatment network.

FIG. 4 shows an exemplary dental treatment network. The device 10 of FIG. 1 transmits operational and dental/medical information while embedded in a patient 1. The data is received by a local processor 99. The local processor 99 in turn uploads the information over a wide area network 102 such as the Internet. The data can be received by a treating professional such as a dentist or an orthodontist at workstation 120. The information can also be sent to one or more diagnostic specialists 130 who review the information and then make recommendation to the treating professional over the network 102. The information can also be sent to the device's manufacturer 110 and any other required dental supplier 140.

An Internet community with one or more dental supply companies, service providers, manufacturers, or marketers is connected to the network 102 and can communicate directly with users of the client workstations 99 or indirectly through the server 100. The Internet community provides the client workstations 99 with access to a network of orthodontic specialists and dental specialists. Additionally, the Internet community also provides access to a variety of supporting members such as financing firms, leasing firms and other service providers, among others.

Although the server 100 can be an individual server, the server 100 can also be a cluster of redundant servers. Such a cluster can provide automatic data failover, protecting against both hardware and software faults. In this environment, a plurality of servers provides resources independent of each other until one of the servers fails. Each server can continuously monitor other servers. When one of the servers is unable to respond, the failover process begins. The surviving server acquires the shared drives and volumes of the failed server and mounts the volumes contained on the shared drives. Applications that use the shared drives can also be started on the surviving server after the failover. As soon as the failed server is booted up and the communication between servers indicates that the server is ready to own its shared drives, the servers automatically start the recovery process. Additionally, a server farm can be used. Network requests and server load conditions can be tracked in real time by the server farm controller, and the request can be distributed across the farm of servers to optimize responsiveness and system capacity. When necessary, the farm can automatically and transparently place additional server capacity in service as traffic load increases.

The server 100 can also be protected by a firewall. When the firewall receives a network packet from the network 102, it determines whether the transmission is authorized. If so, the firewall examines the header within the packet to determine what encryption algorithm was used to encrypt the packet. Using this algorithm and a secret key, the firewall decrypts the data and addresses of the source and destination firewalls and sends the data to the server 100. If both the source and destination are firewalls, the only addresses visible (i.e., unencrypted) on the network are those of the firewall. The addresses of computers on the internal networks, and, hence, the internal network topology, are hidden. This is called "virtual private networking" (VPN).

The server 100 supports a transaction portal that provides a single point of integration, access, and navigation through the multiple enterprise systems and information sources facing knowledge users operating the client workstations 99. The portal can additionally support services that are transaction driven. Once such service is advertising: each time the user accesses the portal, the client workstation 99 downloads information from the server 100. The information can contain commercial messages/links or can contain downloadable software. Based on data collected on users, advertisers may selectively broadcast messages to users. Messages can be sent through banner advertisements, which are images displayed in a window of the portal. A user can click on the image and be routed to an advertiser's Web-site. Advertisers pay for the number of advertisements displayed, the number of times users click on advertisements, or based on other criteria. Alternatively, the portal supports sponsorship programs, which involve providing an advertiser the right to be displayed on the face of the port or on a drop down menu for a specified period of time, usually one year or less and the sponsorship programs enable campaigning and additional business models. The portal also supports performance-based arrangements whose payments are dependent on the success of an advertising campaign, which may be measured by the number of times users visit a Web-site, purchase products or register for services. The portal can refer users to advertisers' Web-sites when they log on to the portal.

Additionally, the portal offers contents and forums providing focused articles, valuable insights, questions and answers, and value-added information about related issues, including information on dental issues. Other services can be supported as well. For example, a user can rent space on the server to enable him/her to download application software (applets) and/or data—anytime and anywhere. By off-loading the storage on the server, the user minimizes the memory required on the client workstation 99, thus enabling complex operations to run on minimal computers such as handheld computers and yet still ensures that he/she can access the application and related information anywhere anytime. Another service is On-line Software Distribution/Rental Service. The portal can distribute its software and other software companies from its server. Additionally, the portal can rent the software so that the user pays only for the actual usage of the software. Such software can include facial modeling software that renders the expected teeth position with the facial image of the patient. After each use, the application is erased and will be reloaded when next needed, after paying another transaction usage fee.

The server 100 allows a consumer to log onto a computerized orthodontic transaction system over a network and automates the steps required to complete a treatment. In addition, information relating to the various portions of a transaction are captured and stored in a single convenient location where it can be accessed at any time.

The system has several benefits and advantages related to patient and user compliance. It provides a means by which the healthcare professional patient or third-party, like a parent, can observe the usage patterns by the patient related to the device delivering cyclic forces in order to accelerate bone remodeling. The elements of compliance that can be tracked include but are not limited to duration of use, frequency of use, confirmation of use by the prescribed patient and not someone else, confirmation of use by the prescribed patient as intended, and any patterns related to misuse or abuse including overuse and underuse. Data analysis as a means of providing rewards or punishment of any form for proper or improper use is also a part of the contemplated system. Adjoining any form of pleasurable activity including listening to music to the use of the system is another benefit. The proposed device can be compatible with any type of analog or digital music player.

The means of data observation by the healthcare professional can be computer-based and compatible with any and all operating systems and software/hardware configurations, or via any other form of electronic media. Facilitation of data upload could be via USB port or any other means of transfer.

The system can be rechargeable or non-rechargeable and can be configured in a manner that would allow either patient mobility or immobility during use. It can be programmed with specific instructions and usage pattern directions by the healthcare professional to ensure safety or for other reasons, and is configured to give the healthcare professional the option of not allowing the patient to have control over the programmed settings.

Data captured can be analyzed by the healthcare professional across any analytical method, approach, or configuration. Data captured can be represented graphically, semantically, or in any other format. Data can be monitored and controlled via the internet.

Another aspect of this system includes a computer implemented system by which active or passive feedback can be provided to the patient. The capability can exist for any data element related to use or misuse to which the healthcare professional will have visibility to be made available to the patient in any graphic, semantic, or other form. Furthermore, the capability can exist for the data in the same aforementioned manner to be made available to the parent or legal guardian of the patient, but not the patient himself. Another feedback contemplation of the current system allows the healthcare professional to real-time track usage by the patient across any data element.

In accordance with the contemplated business aspects of the system, an economic model is created which allows the orthodontic or other healthcare professional office to rent, lease, or sell the system to patients. It can be used as a means of generating profit within the treatment office, or can be passed on to the patient under any agreement without incremental mark-up for any reason, including as a means of promoting the healthcare professional practice. Lease and rental agreements related to the system can be set up with any term structure and can be configured to allow the orthodontist or other healthcare professional discretion as to the pricing and terms of the agreement with the patient or legal guardian of the patient. The system can be leased or rented to the orthodontist or other healthcare professional by the commercializing organization so that it is charged pro rata to any time period increment, especially monthly. The channel strategy used to market the current system can be configured so that the point of sale, rent, or lease is established directly between the commercializing organization and the orthodontic or other healthcare professional office, or it can be established through a leasing company or other third party intermediary, and through any number of such intermediaries.

Through any channel of trade, consumer or professional, volume discounts can be configured, and family or sibling discount programs can be developed for multiple users in a single household. Furthermore, the system contemplates the development of guarantee and warranty programs related to all aspects of the system performance including but not limited to defects and clinical results.

In yet another aspect, components of the system can be recycled, either as a complete unit or at any combination level of components. The benefit of such recycling is that the commercializing organization can establish any number or form of campaigns related to providing rewards to the orthodontist, other healthcare professional, patient, or legal guardian as recycled parts are procured. In the contemplation of a direct-to-consumer product, all aforementioned campaigns and programs can be established with any channel partner or retailer.

Figure 5:
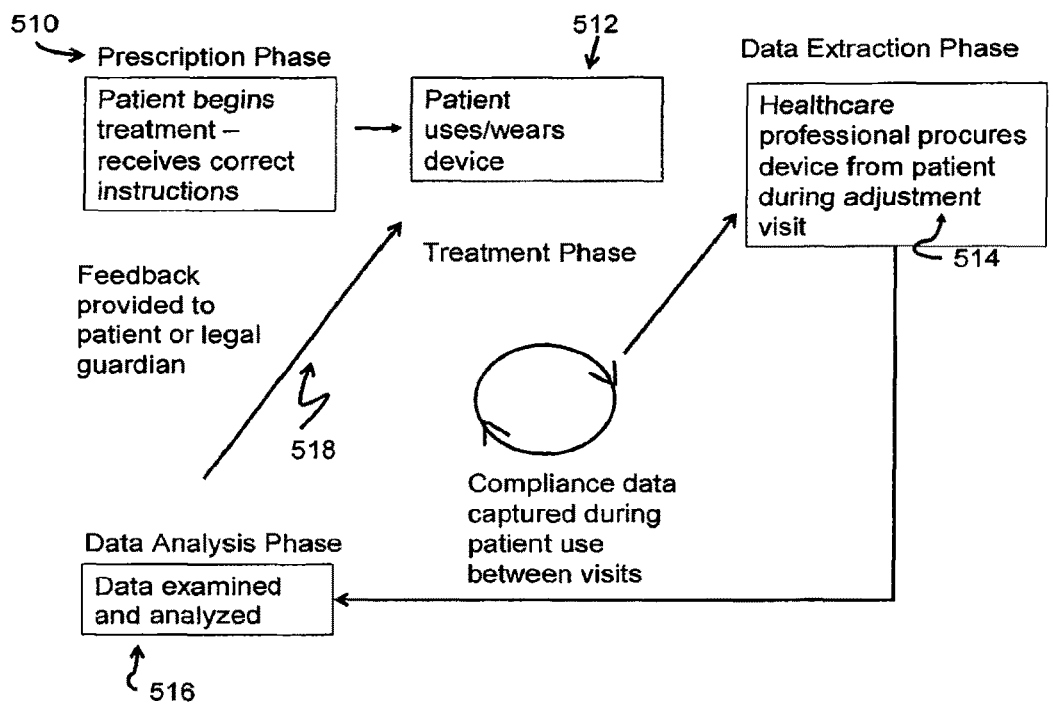
FIG. 5 shows an exemplary process for treating patients using the devices of FIG.

The system improves patient compliance, defined as duration of device use/wear, frequency of device use/wear, consistency in time of day device use/wear, and correct device use/wear such data is captured in data form by the device. Compliance refers to both not overusing and not underusing the device in accordance with the instructions given to the patient by the healthcare professional. This data can be viewed by the healthcare professional, as shown in FIG. 5. In this embodiment, instructions for use and wear are provided to the patient by the healthcare professional (510). The patient uses/wears the device, and data on compliance is captured during patient use (512). After each treatment period, the device is retrieved by the professional and compliance data is extracted therefrom (514). The data is presented in a form that will allow for data analysis by the healthcare professional (516). As a part of an active feedback process (518), the healthcare professional then makes recommendations, or re-prescribes, the device for subsequent use until the next visit or interaction. This process can involve some form of reward or punishment based on the compliance and usage pattern results.

Figure 6:
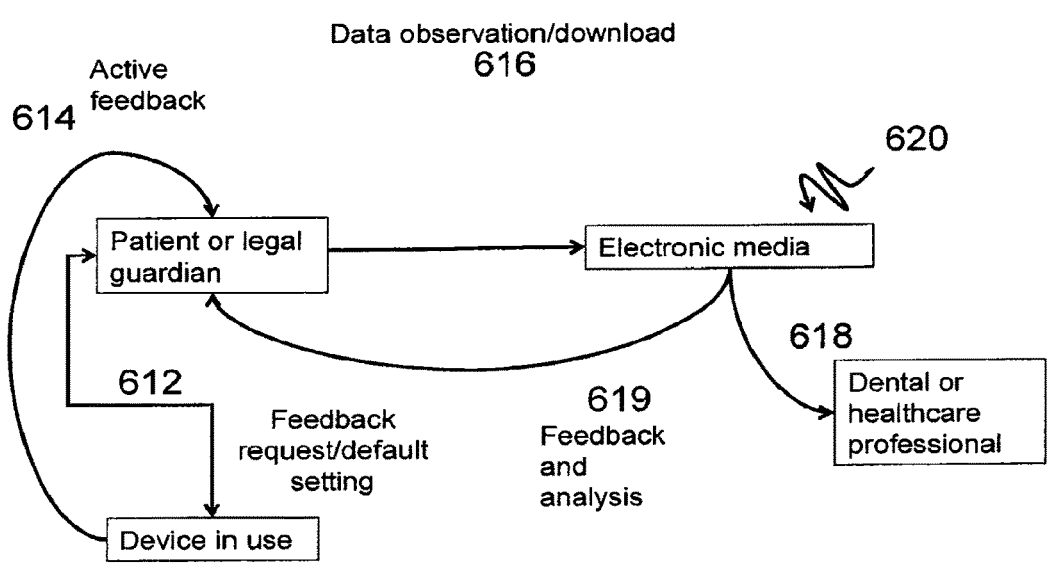
FIG. 6 shows an exemplary process to capture data and provide data for feedback purposes.

As shown in FIG. 6, the data can be provided either directly to the patient or to the legal guardian for feedback purposes as well. The device can be configured as seen in FIG. 6 to provide either active or passive feedback to the patient user. This data generation and observation can be enabled by a request via download with some form of electronic media, or delivered as a default setting during use. For example, during use, the device can provide visual feedback upon request (612) from the patient or automatically (614). The data can be downloaded (616) into an electronic media 620 such as a flash drive and the information can be sent to the professional for feedback and analysis (618), or to the patient directly or to the legal guardian of the patient (619).

Figure 7:
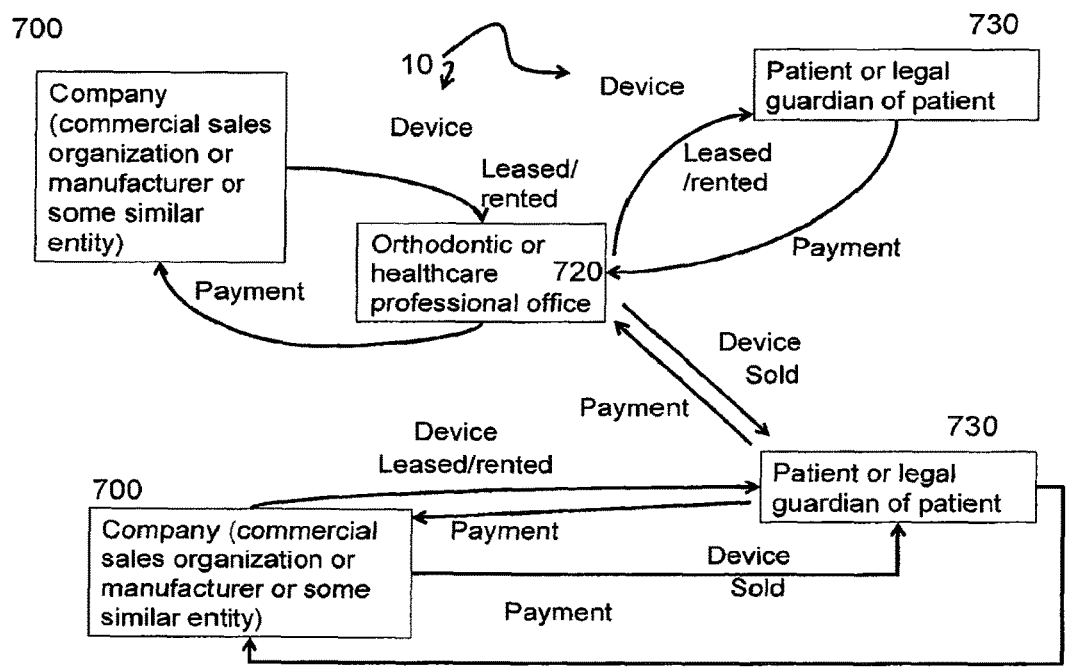
FIG. 7 shows an exemplary system for leasing, renting or purchasing the appliances of FIGS. 1-2.

FIG. 7 demonstrates an exemplary distribution system by company 700 where the device 10 is leased or rented to the patient 730 through the orthodontic office 720, allowing for the patient fee to be proportional to the amount of time that the device is used as a part of the treatment. Alternatively, the patient could rent or lease the device directly from the commercial sales organization or manufacturer as demonstrated in FIG. 7. The patient could also purchase the appliance instead of leasing or renting the device 10, either from the orthodontic or healthcare professional office 720 or from the commercial sales organization or manufacturer 700.

Figure 8:
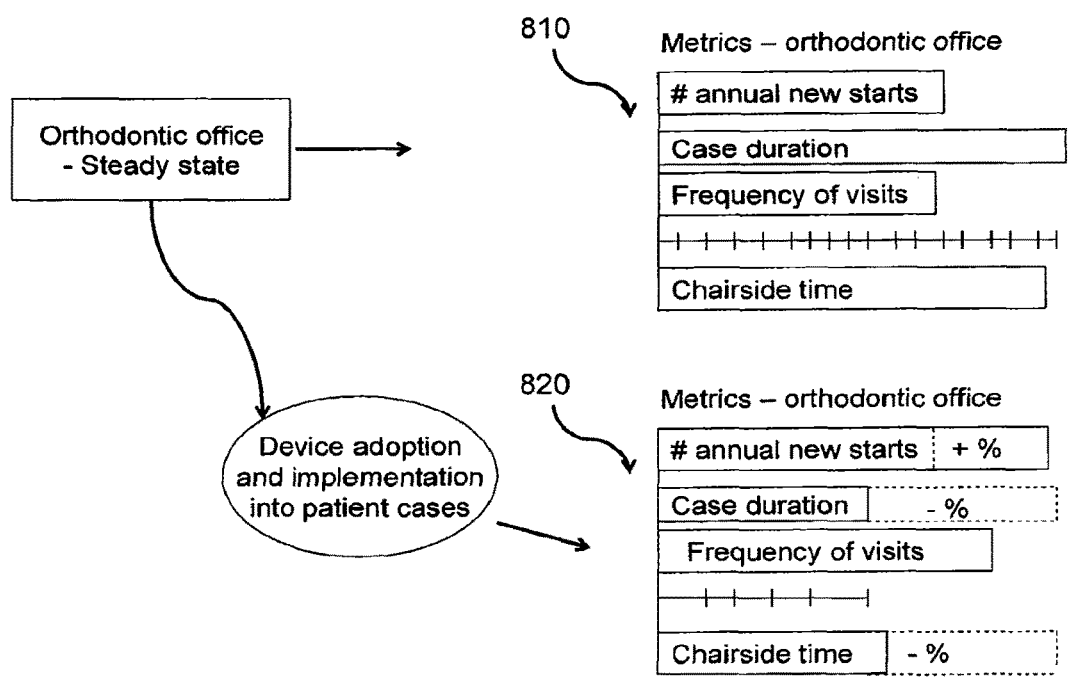
FIG. 8 shows an exemplary process for improving office and case efficiency.

An additional aspect of the proposed system is related to the efficiency improvement that it allows and enables within the orthodontic or other healthcare professional office. It can be used to decrease treatment duration times, increase the number of new starts, improve financial performance of the practice across any metric, attract new patients, recruit former treatment-rejecters, and improve relations with upstream or downstream referring or referral dental/medical professionals of any discipline or specialty. Healthcare professional efficiency increases as a result of patients using the system. This improvement could include metrics such as an increased number of new case starts, a shorter duration of total treatment time, frequency of recall or adjustment visits, or a decreased amount of chairside time, as shown in FIG. 8. In FIG. 8, the orthodontic office exists in a steady state in office and case efficiency without the device (810). As the adoption of the technology is increased and the devices are incorporated into patient cases, an improvement in the office and case efficiency is achieved (820). These efficiency improvements can occur as a part of or as a result of any stage of orthodontic treatment of any malocclusion classification, and with any archwire or appliance type, including all wire sizes, shapes, and compositions.

Figure 9:
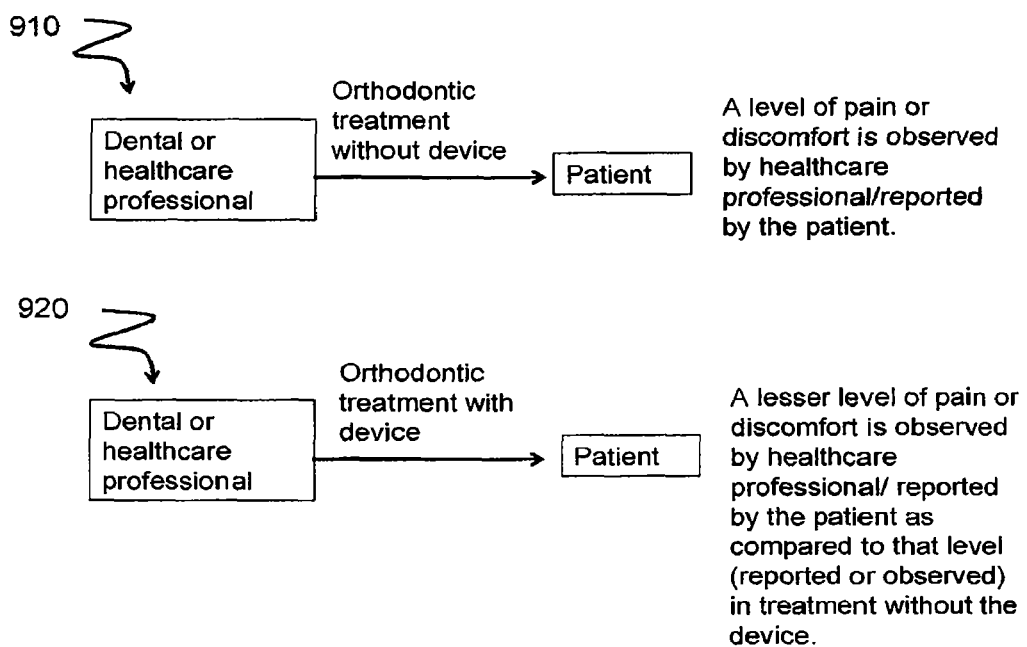
FIGS. 9-10 show an exemplary process to compare differences in pain level for patients treated with and without the appliances of FIGS. 1-2.
Figure 10:
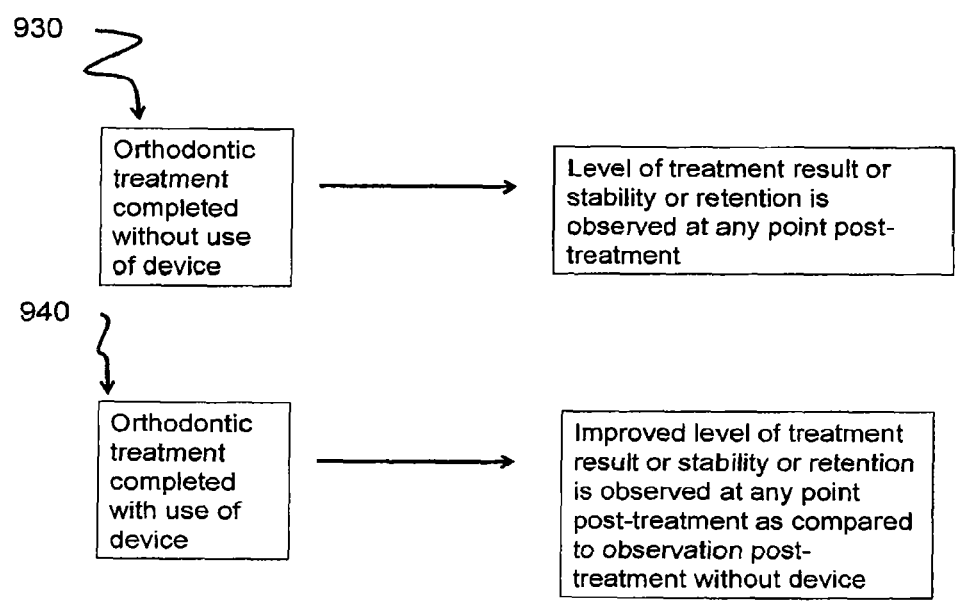

FIGS. 9-10 show an exemplary process to compare differences in pain level and integrity of clinical outcomes, respectively, for patients treated with and without the appliances of FIG. 1 or FIG. 2. FIG. 9 demonstrates a decrease in patient pain and discomfort as a result of using the device while FIG. 10 demonstrates an improvement in treatment outcomes as a result of this device. In FIG. 9, the healthcare professional treats the patient without the device of the present invention (910) and the level of pain and/or discomfort is observed by the treating professional or reported by the patient. The healthcare professional then treats the patient with the device of the present invention and the level of pain and/or discomfort is observed by the treating professional or reported by the patient is captured (920). The difference between the pain level in patients treated with or without the device can be analyzed. The device treats patient with less pain, and the treatment result could be in the form of improved tissue integrity. The improved result could be observed immediately following the treatment or indefinitely into the future beyond the end of the treatment. The corresponding operations 930 and 940 are shown in FIG. 10.

Figure 11:
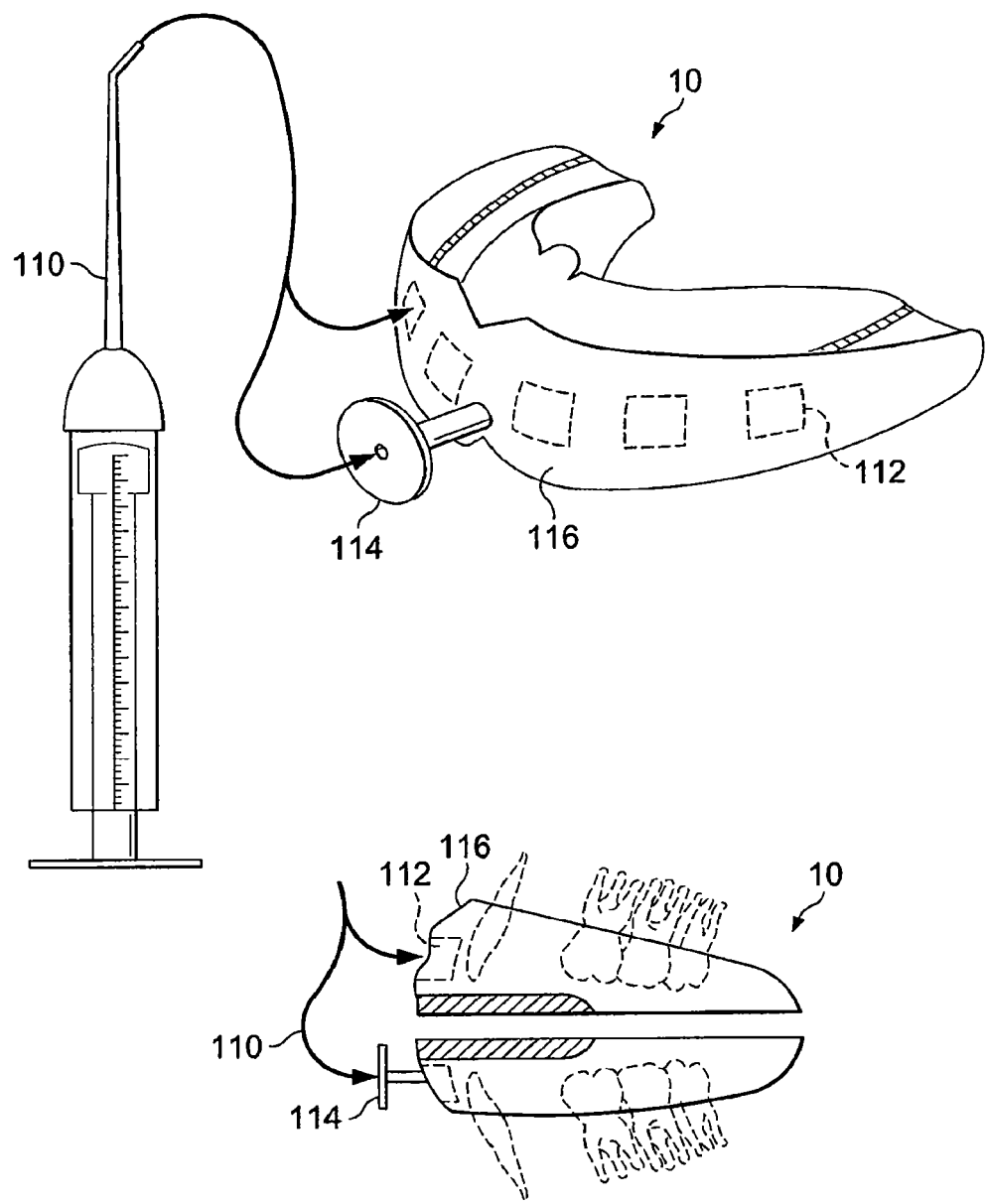
FIG. 11 shows an embodiment for the orthodontic treatment system in which the device is used as a bleaching or tooth-whitening adjunctive with the appliance of FIGS. 1-2.

FIG. 11 represents an adjunctive procedure or usage application that involves the delivery of teeth-whitening or bleaching agents to the teeth with the previous appliance contemplated to deliver non-static forces to the dentition. Some bleaching agent 110 is dispensed either directly into pre-formed reservoirs 112 or some other form of agent-holding and delivery function, or into a pump apparatus 114 that can be depressed to deliver the agent as desired. It is understood that the bleaching agent can be of any composition or concentration and can be purchased directly by the consumer or prescribed by the dental professional. It is further understood that the design and number of reservoirs can be of any nature. FIG. 11 demonstrates one embodiment in which the reservoirs 112 are located on the insides of the facial flange 116 of the device so that they are spatially in contact with the facial surfaces of the maxillary anterior dentition. The bleaching agent can interact directly with the dental tissue and can also percolate through the orthodontic appliances so that it is delivered even underneath the brackets.

Figure 12:
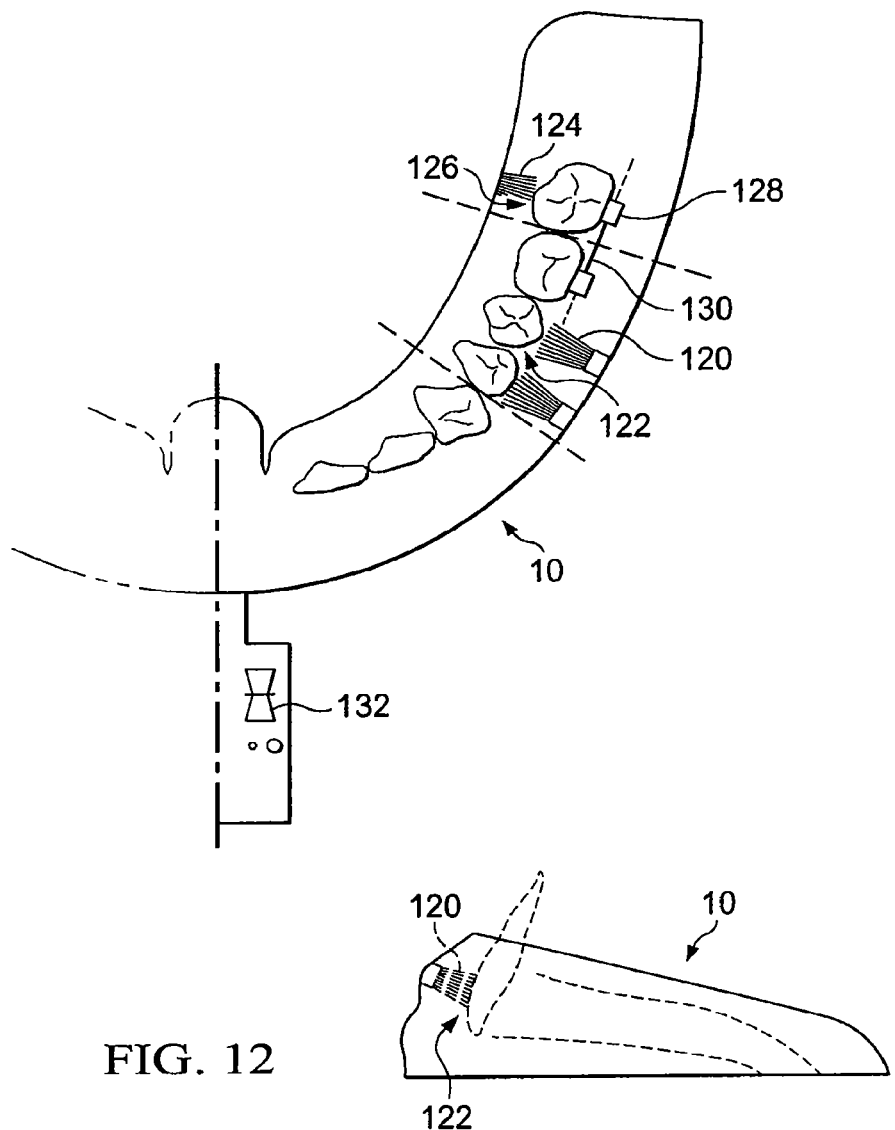
FIG. 12 shows an embodiment for the orthodontic treatment system in which the device is used as a tooth-brushing or prophylactic apparatus adjunctive with the appliance of FIGS. 1-2.

FIG. 12 represents an embodiment that allows for an adjunctive application related to inducing accelerated tooth movement as well as cleaning the teeth or orthodontic appliances. The cleaning mechanism is mechanical in nature and involves bristles or some similar component removing plaque bacteria. Possible forms include an embodiment of the device 10 with a tuft(s) of bristles 120 coming into contact with the facial surface(s) of the dentition 122. The cleaning tufts can include bristles of any form, composition, number, and arrangement. Furthermore, it is understood that a tuft can interact with a single tooth or can span more than a single tooth. Similarly, tufts 124 can be arranged on the lingual side of the bite plate apparatus and come into contact with the lingual surfaces 126 of the teeth. The bristles can interface directly with the teeth or with the orthodontic appliances, especially the brackets 128 and the archwire 130. The brushing action can be activated either automatically upon the sensing of some stimuli such as bite pressure, moisture, or temperature, or can be activated manually via depressing a button 132 that is located in this particular representation extraorally. It is understood that the ratio and location of bristles or like functional components can be customized to fit a particular patient.

Expanded indications and applications related to the current system include pain reduction and improved clinical results through improved tissue and bone integrity. The contemplated reduction of pain applies to initial adjustments during orthodontic visits, ongoing discomfort levels between orthodontic visits, and post-treatment with any dentofacial surgery procedure, including trauma and correction of any form. Levels of discomfort are typically the highest immediately post-adjustment because the tension that is lost due the movement of teeth is recovered by tightening the archwire. The current system intermittently increases and then releases this constant pressure at a high frequency. The resulting perception to the patient is less pain and less discomfort. This observation is partially due to the fact that the device distracts the patient's attention away from the pain; but it is also a result of the subtle release of pressure with the back half of each cycle as the bite plate or platform comes out of contact with the dentition.

The contemplated tissue integrity improvement is related to any component of the periodontium: alveolar bone, periodontal ligament (PDL), cementum tissue, and gingivae. Such a bone integrity and related density improvement also extends to all other dentofacial bone applications, including bone-healing applications related to the treatment of trauma. The benefit of such an improvement allows for a more stable result with a higher degree of treatment retention and resulting less treatment relapse as related to the teeth remaining in their post-treatment position as opposed to migrating back to their pre-treatment positions. Patients with improved bone density and tissue integrity do not have to follow the post-treatment retention and retainer regimens that are as rigid. From a functional and structural perspective, over time the occlusion of the upper and lower arches then generates less unnecessary wear to the surfaces of the teeth because the supporting bone and other tissue structures are stronger and provide a steady foundation. A stronger periodontium also has the benefit of more stable overall oral health.

The above system is advantageous in providing improvement of patient compliance, development of a leasing business model, improvement of healthcare professional office efficiency, and enhancement of treatment outcomes through reduced pain and stronger tissue and stability. The device utilizes the application of non static forces. Said forces can be cyclic in nature and application. Malocclusion refers to the misalignment of teeth and/or incorrect relation between the teeth of the two dental arches. Patient compliance involves behavior as it relates to following treatment instructions and recommendations given by the healthcare professional. In one embodiment, the proposed system would be rented through a leasing business model to patients through healthcare professional offices as an intermediary, and serve as a means of increasing office throughput and efficiency. The system designed as a medical device in this way decreases patient pain and discomfort and improves tissue integrity and clinical results.

The invention has been described herein in considerable detail to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself. It will be recognized by those skilled in the art that changes may be made to the above-described embodiments of the system without departing from the broad inventive concepts thereof. It is understood therefore, that this system is not limited to the particular embodiment disclosed, but is intended to cover any modifications that are within the scope and spirit of the system as defined by the appended claims.

What is claimed is:

1. A method for correcting malocclusion, comprising: reducing orthodontic treatment duration by daily applying cyclic forces simultaneously to teeth of the maxillary and mandibular arches during a treatment period, the teeth also receiving static forces generated by an orthodontic appliance during the treatment period, the cyclic forces applied daily by:
   clamping the teeth down on a bite plate;
   activating an extraoral vibration source configured to deliver the cyclic forces to the bite plate at a constant frequency in a range of 0.1 to 400 Hertz and a maximum force;
   wherein the bite plate and the extraoral vibration source are held during use only by clamping the teeth on the bite plate; and
   storing, electronically, data indicating usage duration and usage frequency.

2. The method of claim 1 wherein the usage data is readable to determine patient compliance.

3. The method of claim 1 wherein the orthodontic appliance is braces.

4. The method of claim 1 wherein the orthodontic appliance is a clear aligner.

5. The method of claim 1 wherein the constant frequency is about 40 Hertz.

6. The method of claim 1 wherein the cyclic forces are applied about 20 minutes daily.

7. The method of claim 1 wherein the maximum force is about 5 Newtons.

8. The method of claim 1 further comprising automatically deactivating the extraoral vibration source after a predetermined time.

9. The method of claim 1 further comprising activating an indicator upon elapse of a predetermined usage duration.

10. The method of claim 1 wherein the treatment period begins with bonding of brackets to at least some of the teeth and ends with removal of the brackets.

11. A method for correcting malocclusion, comprising:
    accelerating movement of teeth during an orthodontic treatment period by daily applying cyclic forces simultaneously to teeth of the maxilla and mandible arches during the orthodontic treatment period, the teeth also receiving static forces generated by an orthodontic appliance during the orthodontic treatment period, the cyclic forces applied daily by:
    clamping the teeth down on a bite plate;
    activating an extraoral vibration source configured to deliver the cyclic forces to the bite plate at a constant frequency in a range of 0.1 to 400 Hertz and a maximum force; and
    storing, electronically, data indicating usage duration and usage frequency.

12. The method of claim 11 wherein the usage data is readable to determine patient compliance.

13. The method of claim 11 wherein the orthodontic appliance is braces.

14. The method of claim 11 wherein the orthodontic appliance is a clear aligner.

15. The method of claim 11 wherein the constant frequency is about 40 Hertz.

16. The method of claim 11 wherein the cyclic forces are applied about 20 minutes daily.

17. The method of claim 11 wherein the maximum force is about 5 Newtons.

18. The method of claim 11 further comprising automatically deactivating the extraoral vibration source after a predetermined time.

19. The method of claim 11 further comprising activating an indicator upon elapse of a predetermined usage duration.

20. The method of claim 11 wherein the treatment period begins with bonding of brackets to at least some of the teeth and ends with removal of the brackets.

* * * * *